United States Patent
McCollough et al.

(10) Patent No.: US 11,517,278 B2
(45) Date of Patent: Dec. 6, 2022

(54) SYSTEM AND METHOD FOR BASIS MATERIAL DECOMPOSITION WITH GENERAL PHYSICAL CONSTRAINT FOR MULTI-ENERGY COMPUTED TOMOGRAPHY

(71) Applicant: Mayo Foundation for Medical Education and Research, Rochester, MN (US)

(72) Inventors: Cynthia H. McCollough, Byron, MN (US); Shuai Leng, Rochester, MN (US); Zhoubo Li, Libertyville, IL (US); Lifeng Yu, Byron, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 210 days.

(21) Appl. No.: 16/753,873

(22) PCT Filed: Oct. 8, 2018

(86) PCT No.: PCT/US2018/054855
§ 371 (c)(1),
(2) Date: Apr. 6, 2020

(87) PCT Pub. No.: WO2019/071256
PCT Pub. Date: Apr. 11, 2019

(65) Prior Publication Data
US 2020/0281552 A1   Sep. 10, 2020

Related U.S. Application Data

(60) Provisional application No. 62/568,988, filed on Oct. 6, 2017.

(51) Int. Cl.
*A61B 6/00* (2006.01)
*G16H 30/40* (2018.01)
*G06T 11/00* (2006.01)

(52) U.S. Cl.
CPC ............ *A61B 6/482* (2013.01); *G06T 11/008* (2013.01); *G16H 30/40* (2018.01); *G06T 2211/408* (2013.01)

(58) Field of Classification Search
CPC ............... G01N 23/087; G01N 23/046; G01N 2223/206
See application file for complete search history.

(56) References Cited

U.S. PATENT DOCUMENTS

2017/0328844 A1* 11/2017 Li .................... G01N 23/087

FOREIGN PATENT DOCUMENTS

WO   2009102996 A2   8/2009
WO   2016171570 A1   10/2016

OTHER PUBLICATIONS

Petrongolo, et al, "A general framework of noise suppression in material decomposition for dual-energy CT," Med Phys 42, 4848-4862 (2015).

(Continued)

*Primary Examiner* — Dani Fox
(74) *Attorney, Agent, or Firm* — Quarles & Brady LLP

(57) ABSTRACT

A system and method is provided for performing material decomposition using a computed tomography (CT) system. The method includes acquiring CT imaging data of an object including data subsets corresponding to at least two different energy spectral bins and using the CT imaging data at each of the at least two different energy spectral bins to form a series of equations for basis material decomposition. The method also includes using a general physical constraint, which quantifies how each basis material in the object is (Continued)

mixed together to form the object, within the series of equations. The method also includes determining at least one basis material density of the object using the physical constraint and the CT imaging data and generating an image of the object using the CT imaging data and the mass densities of at least one basis material.

8 Claims, 4 Drawing Sheets

(56) References Cited

OTHER PUBLICATIONS

Primak, A. N., et al. "Improved dual-energy material discrimination for dual-source CT by means of additional spectral filtration." Medical physics 36.4 (2009): 1359-1369.
Primak, A.N., et al., Noninvasive Differentiation of Uric Acid versus Non-Uric Acid Kidney Stones Using Dual-Energy CT. Academic Radiology, 2007. 14(12): p. 1441-1447.
Qu, M., et al., Toward Biphasic Computed Tomography (CT) Enteric Contrast: Material Classification of Luminal Bismuth and Mural Iodine in a Small-Bowel Phantom Using Dual-Energy CT. Journal of Computer Assisted Tomography, 2012. 36(5): p. 554-559.
Ren, L., et al, Tutorial on X-ray photon counting detector characterization. Journal of X-ray science and technology, 2018. 26(1): p. 1-28.
Ren, L., et al. Three-material decomposition in multi-energy CT: impact of prior information on noise and bias, in SPIE Medical Imaging. 2018. SPIE.
Roessl, E. et al, K-edge imaging in x-ray computed tomography using multi-bin photon counting detectors. Physics in Medicine & Biology, 2007. 52(15): p. 4679.
Roessl, E. et al, Cramér-Rao lower bound of basis image noise in multiple-energy x-ray imaging. Physics in Medicine & Biology, 2009. 54(5): p. 1307.
Schlomka, et al, "Experimental feasibility of multi-energy photon-counting K-edge imaging in pre-clinical computed tomography," Phys Med Biol 53, 4031-4047 (2008).
Sfeir, J.G., et al., Evaluation of cross-sectional and longitudinal changes in volumetric bone mineral density in postmenopausal women using single- versus dual-energy quantitative computed tomography. Bone, 2018. 112: p. 145-152.
Silva et al, Dual-Energy (Spectral)CT: Applications in Abdominal Imaging. Radiographics 2011.
Slinger, C. W., et al. "Adaptive coded aperture imaging in the infrared: towards a practical implementation." Adaptive Coded Aperture Imaging and Non-Imaging Sensors II. vol. 7096. International Society for Optics and Photonics, 2008.
Sommer, W.H., et al., Image Quality of Virtual Noncontrast Images Derived from Dual-energy CT Angiography after Endovascular Aneurysm Repair. Journal of Vascular and Interventional Radiology, 2010. 21(3): p. 315-321.
Stamatelou, K. K., et al. "Time trends in reported prevalence of kidney stones in the United States: 1976-1994." Kidney international 63.5 (2003): 1817-1823.
Sukovic, P. et al. Basis material decomposition using triple-energy X-ray computed tomography, in IMTC/99. Proceedings of the 16th IEEE Instrumentation and Measurement Technology Conference (Cat. No. 99CH36309). 1999.
Symons, R., et al., Photon-counting CT for simultaneous imaging of multiple contrast agents in the abdomen: An in vivo study. Medical Physics, 2017. 44(10): p. 5120-5127.
Wang, A.S. et al. A comparison of dual kV energy integrating and energy discriminating photon counting detectors for dual energy x-ray imaging. in SPIE Medical Imaging. 2012. SPIE.
Wang, A.S., et al., Pulse pileup statistics for energy discriminating photon counting x-ray detectors. Medical Physics, 2011. 38(7): p. 4265-4275.

Xue, Y., et al., Statistical image-domain multimaterial decomposition for dual-energy CT. Medical Physics, 2017. 44(3): p. 886-901.
Yu, et al, "Pre-reconstruction three-material decomposition in dualenergy CT," in Medical Imaging 2012 (International Society for Optics and Photonics, 2009), pp. 72583V-72583V-72588.
Yu, et al, "Virtual monochromatic imaging in dual-source dual-energy CT: radiation dose and image quality," Med Phys 38, 6371-6379 (2011).
Yu, L., et al, Dual-Energy CT-Based Monochromatic Imaging. American Journal of Roentgenology, 2012. 199(5_supplement): p. S9-S15.
Yu, L., et al. Dual-source multi-energy CT with triple or quadruple x-ray beams, in SPIE Medical Imaging. 2016. SPIE.
Yu, Z., et al. Initial results from a prototype whole-body photon-counting computed tomography system. in SPIE Medical Imaging. 2015. SPIE.
Yu, Z., et al., Evaluation of conventional imaging performance in a research whole-body CT system with a photon-counting detector array. Physics in Medicine & Biology, 2016. 61(4): p. 1572.
Yuan, et al, "Reduced Iodine Load at CT Pulmonary Angiography with Dual-Energy Monochromatic Imaging: Comparison with Standard CT Pulmonary Angiography—A Prospective Randomized Trial," Radiology 262, 290-297 (2012).
Yveborg, M., et al, Theoretical Comparison of a Dual Energy System and Photon Counting Silicon Detector Used for Material Quantification in Spectral CT. IEEE Transactions on Medical Imaging, 2015. 34(3): p. 796-806.
Zhang, et al, "Liver virtual non-enhanced CT with dual-source, dual-energy CT: a preliminary study," Eur Radiol 20, 2257-2264 (2010).
Zhao, W., et al. Energy spectrum extraction and optimal imaging via dual-energy material decomposition, in 2015 IEEE Nuclear Science Symposium and Medical Imaging Conference (NSS/MIC). 2015.
Zhao, W., et al., Using edge-preserving algorithm with non-local mean for significantly improved image-domain material decomposition in dual-energy CT. Physics in Medicine & Biology, 2016. 61(3): p. 1332.
Agnew, "Rescaled Specific Volume Model for Electrolyte Solution Density," J Chem Eng Data 57, 60-65 (2012).
Alvarez, "Estimator for photon counting energy selective x-ray imaging with multibin pulse height analysis," Med Phys 38, 2324-2334 (2011).
Alvarez, R.E. et al. Energy-selective reconstructions in X-ray computerised tomography. Physics in Medicine & Biology, 1976. 21(5): p. 733.
Bauer, R.W., et al., Dual-Energy CT for the Assessment of Chronic Myocardial Infarction in Patients With Chronic Coronary Artery Disease: Comparison With 3-T MRI. American Journal of Roentgenology, 2010. 195(3): p. 639-646.
Bornefalk, H. et al, Theoretical Comparison of the Iodine Quantification Accuracy of Two Spectral CT Technologies. IEEE Transactions on Medical Imaging, 2014. 33(2): p. 556-565.
Buerke, et al., "Dual-Energy CTA with Bone Removal for Transcranial Arteries: Intraindividual Comparison with Standard CTA without Bone Removal and TOF-MRA," Acad Radiol 16, 1348-1355 (2009).
Cann, C.E., Quantitative CT for determination of bone mineral density: a review. Radiology, 1988. 166(2): p. 509-522.
Cho, H.M., et al., Calibration phantoms for accurate water and lipid density quantification using dual energy mammography. Physics in Medicine & Biology, 2017. 62(11): p. 4589.
Choi, et al, "Dual energy computed tomography in tophaceous gout," Ann Rheum Dis 68, 1609-1612 (2009).
Clark, D.P., et al. Multi-energy CT decomposition using convolutional neural networks. in SPIE Medical Imaging. 2018. SPIE.
Curtis, T.E. et al, Effects of calibration methods on quantitative material decomposition in photon-counting spectral computed tomography using a maximum a posteriori estimator. Medical Physics, 2017. 44(10): p. 5187-5197.
Dangelmaier, J., et al., Experimental feasibility of spectral photon-counting computed tomography with two contrast agents for the detection of endoleaks following endovascular aortic repair. European Radiology, 2018.

(56) References Cited

OTHER PUBLICATIONS

Duan, et al, "CT scanner x-ray spectrum estimation from transmission measurements," Med Phys 38, 993-997 (2011).

Faby, S., et al., Performance of today's dual energy CT and future multi energy CT in virtual non-contrast imaging and in iodine quantification: A simulation study. Medical Physics, 2015. 42(7): p. 4349-4366.

Fischer, et al, "Quantification of Liver Fat in the Presence of Iron and Iodine an Ex- Vivo Dual-Energy CT Study," Invest Radiol 46, 351-358 (2011).

Fornaro, J., et al., Dual- and multi-energy CT: approach to functional imaging. Insights into Imaging, 2011. 2(2): p. 149-159.

Fung, G.S.K., et al. XCAT/DRASIM: a realistic CT/human-model simulation package. in SPIE Medical Imaging. 2011. SPIE.

Glazebrook, et al., "Identification of Intraarticular and Periarticular Uric Acid Crystals with Dual-Energy CT: Initial Evaluation," Radiology 261, 516-524 (2011).

Goldberg, et al, "Noninvasive quantitation of liver iron in dogs with hemochromatosis using dual-energy CT scanning," Invest Radiol 17, 375-380 (1982).

Graser, et al, "Dual energy CT characterization of urinary calculi: Initial in vitro and clinical experience," Invest Radiol 43, 112-119 (2008).

Graser, et al, "Dual-Energy CT in Patients Suspected of Having Renal Masses: Can Virtual Nonenhanced Images Replace True Nonenhanced Images?," Radiology 252, 433-440 (2009).

Hassler, et al, "X-ray dual-energy calibration based on estimated spectral properties of the experimental system," Ieee T Nucl Sci 45, 1699-1712 (1998).

International Searching Authority, International Search Report and Written Opinion for application PCT/US2018/054855. dated Jan. 24, 2019.

Johnson, T.R.C., et al., Material differentiation by dual energy CT: initial experience. European Radiology, 2007. 17(6): p. 1510-1517.

Kappler, S., et al. Photon counting CT at elevated X-ray tube currents: contrast stability, image noise and multi-energy performance, in SPIE Medical Imaging. 2014. SPIE.

Kelcz, F., et al., Noise considerations in dual energy CT scanning. Medical Physics, 1979. 6(5): p. 418-425.

Krauss B., et al., Dual Source CT, in Dual Energy CT in Clinical Practice, F.C. Johnson T., Schönberg S., Reiser M., Editor. 2011, Springer: Berlin, Heidelberg p. 11-20.

Laliberte, et al, "Model for calculating the density of aqueous electrolyte solutions," J Chem Eng Data 49, 1141-1151 (2004).

Lam E.J., et al, "A model for calculating the density of aqueous multicomponent electrolyte solutions," J Chil Chem Soc 53, 1393-1398 (2008).

Lee, et al, "Quantitative material decomposition using spectral computed tomography with an energy-resolved photon-counting detector," Phys Med Biol 59, 5457-5482 (2014).

Lehmann, L.A., et al., Generalized image combinations in dual KVP digital radiography. Medical Physics, 1981. 8(5): p. 659-667.

Leng, S. et al, "Maximizing Iodine Contrast-to-Noise Ratios in Abdominal CT Imaging through Use of Energy Domain Noise Reduction and Virtual Monoenergetic Dual-Energy CT," Radiology 276, 562-570 (2015).

Leng, S. et al. "Noise reduction in spectral CT: Reducing dose and breaking the trade-off between image noise and energy bin selection." Medical physics 38.9 (2011): 4946-4957.

Li, et al, "A new generalized model for predicting the density of single- and mixed-electrolyte solutions," Fluid Phase Equilibr 145, 1-14 (1998).

Li, et al, "Dual-Energy Computed Tomography Imaging of Thyroid Nodule Specimens Comparison With Pathologic Findings," Invest Radiol 47, 58-64 (2012).

Li, et al, "Iodine quantification with dual-energy CT: phantom study and preliminary experience with VX2 residual tumour in rabbits after radiofrequency ablation," Brit J Radiol 862013). 2013.

Li, Zhoubo, et al. "Image-based material decomposition with a general volume constraint for photon-counting CT." Medical Imaging 2015: Physics of Medical Imaging. vol. 9412. International Society for Optics and Photonics, 2015.

Liu, X., et al., Quantitative imaging of element composition and mass fraction using dual-energy CT: Three-material decomposition. Medical Physics, 2009. 36(5): p. 1602-1609.

Macovski, et al, "Energy dependent reconstruction in X-ray computerized tomography," Comput Biol Med 6, 325-336 (1976).

Malusek, A., et al., The potential of dual-energy computed tomography for quantitative decomposition of soft tissues to water, protein and lipid in brachytherapy. Physics in Medicine & Biology, 2013. 58(4): p. 771.

McCollough, C.H., et al., Dual- and Multi-Energy CT: Principles, Technical Approaches, and Clinical Applications. Radiology, 2015. 276(3): p. 637-653.

Mendonça, P.R.S., et al, A Flexible Method for Multi-Material Decomposition of Dual-Energy CT Images. IEEE Transactions on Medical Imaging, 2014. 33(1): p. 99-116.

Meola, J., et al. "Image misregistration effects on hyperspectral change detection." Algorithms and Technologies for Multispectral, Hyperspectral, and Ultraspectral Imagery XIV. vol. 6966. International Society for Optics and Photonics, 2008.

Moe, O. W. "Kidney stones: pathophysiology and medical management." The lancet 367.9507 (2006): 333-344.

Mongan, J., et al., In Vivo Differentiation of Complementary Contrast Media at Dual-Energy CT. Radiology, 2012. 265(1): p. 267-272.

Muenzel, D., et al. Photon counting CT of the liver with dual-contrast enhancement. in SPIE Medical Imaging. 2016. SPIE.

Muenzel, D., et al., Simultaneous dual-contrast multi-phase liver imaging using spectral photon-counting computed tomography: a proof-of-concept study. European Radiology Experimental, 2017. 1(1): p. 25.

Muenzel, D., et al., Spectral Photon-counting CT: Initial Experience with Dual-Contrast Agent K-Edge Colonography. Radiology, 2017. 283(3): p. 723-728.

Nicolaou, et al, "Dual-Energy CT as a Potential New Diagnostic Tool in the Management of Gout in the Acute Setting," Am J Roentgenol 194, 1072-1078 (2010).

Niu, T., et al., Iterative image-domain decomposition for dual-energy CT. Medical Physics, 2014. 41(4): p. 041901-n/a.

\* cited by examiner

SYSTEM AND METHOD FOR BASIS MATERIAL DECOMPOSITION WITH GENERAL PHYSICAL CONSTRAINT FOR MULTI-ENERGY COMPUTED TOMOGRAPHY

CROSS-REFERENCE TO RELATED APPLICATIONS

This application is a 371 U.S. National Phase application of PCT/US2018/054855, filed Oct. 8, 2018, which claims the benefit of U.S. Provisional Patent Application Ser. No. 62/568,988 filed on Oct. 6, 2017, and entitled "System and Method for Basis Material Decomposition with a General Physical Constraint for Multi-Energy Computed Tomography," each of which is herein incorporated by reference in its entirety.

STATEMENT REGARDING FEDERALLY SPONSORED RESEARCH

This invention was made with government support under EB016966 awarded by the National Institutes of Health. The government has certain rights in the invention.

BACKGROUND

The present disclosure relates to medical imaging, industrial CT, and small animal imaging. More particularly, the present disclosure relates to systems and methods for basis material decomposition, for example, by using a general physical constraint and multi-energy CT (MECT) data.

In a computed tomography system, at least one x-ray source projects a beam that is collimated to lie within an X-Y plane of a Cartesian coordinate system, termed the "imaging plane." The x-ray beam passes through the object being imaged, such as a medical patient or other non-medical patient or object, such as in industrial CT imaging, and impinges upon an array of radiation detectors. The intensity of the transmitted radiation is dependent upon the strength of the unattenuated beam emerging from the x-ray source (i.e., the applied radiation dose) and the attenuation of the x-ray beam by the object. Each detector produces a separate electrical signal that is a measurement of the attenuated beam. The attenuation measurements from all the detectors are acquired separately to produce the transmission profile at a particular view angle.

The source and detector array in a conventional CT system are rotated on a gantry within the imaging plane and around the object so that the angle at which the x-ray beam intersects the object constantly changes. A group of x-ray attenuation measurements from the detector array at a given angle is referred to as a "view", and a "scan" of the object comprises a set of views acquired at different angular orientations during one revolution of the x-ray source and detector. In a 2D scan, data is processed to construct an image that corresponds to a two dimensional slice taken through the object. The prevailing method for reconstructing an image from 2D data is referred to in the art as the filtered backprojection technique, however, other image reconstruction processes are also well known. This process converts the attenuation measurements from a scan into integers called "CT numbers", which are used to control the brightness of a corresponding pixel on a display.

Recent advances in multi-energy CT (MECT) have enabled the evaluation of material attenuation property at different X-ray spectra, from which quantitative material composition analysis can be performed to create material specific images. This process is referred to as "material decomposition."

Material decomposition can be performed directly on the CT projection data, solving the line integrals of each basis material and reconstructing images from those material-specific line integrals. This method is referred to as a "projection-based" decomposition method. Alternatively, the CT data can be reconstructed into images and the material decomposition can be performed as an "image-based" decomposition method. Recently, many iterative reconstruction methods were proposed to perform material decomposition during reconstruction process.

Both projection- and image-based methods frequently require accurate knowledge of x-ray spectrum, scanner geometry, and detector response information, which are proprietary information that is only available to the manufacturer of the CT system. Some have done substantial empirical studies to published methods that estimate the spectrum from transmission measurements. However, the accuracy of the estimated spectrum is questionable and is, at best, only reliable contemporaneously with the empirical analysis. For example, both spectra and detector response might drift over time due to the aging of components, such as sputtering of anode material on the tube window, which would appreciably change the estimated spectrum over time. Moreover, such measurements require specialized instruments and techniques and can be very time-consuming in a clinical environment.

In dual-energy CT (DECT), material decomposition methods frequently assume volume conservation, allowing three basis materials to be decomposed from two energy measurements. In multi-energy CT (MECT) with energy bins more than 2, such as energy resolved photon-counting CT, although the number of energy measurements are sufficient to solve more than 2 basis materials, additional constraint such as volume conservation is still needed to improve noise properties. In addition, for materials without a measurable k-edge, interactions between X-rays and matter are limited to photoelectric and Compton effects, which limit the analysis to only two basis materials for material decomposition, although more than two energy measurements are available. To enable more than two basis materials, some have attempted to use volume conservation. However, volume conservation is often violated in solutions or mixtures. Errors in presumed volume conservation can lead to bias in material quantification.

SUMMARY

The present disclosure overcomes the aforementioned drawbacks by providing a system and method for basis material decomposition that utilizes a general condition on physical constraint of material mixture that does not require the volume to be conserved. This general physical constraint can either be represented as an unknown variable, which can be solved directly from multi-energy measurements, or obtained from reference data. The reference data can be created based available information or empirical measurements to determine how the basis materials mix in the object. Thus, the present disclosure can reduce the bias compared to volume conservation methods and, in the case of utilizing reference data, provide an improved image quality (e.g. reduced noise or artifacts) in material decomposition.

In one configuration, a method is provided for performing material decomposition using a computed tomography (CT)

system. The method includes acquiring CT imaging data of an object including data subsets corresponding to at least two different energy spectral bins or spectra and using the CT imaging data at each of the at least two different energy spectral bins or spectra to form a series of equations for basis material decomposition. The method also includes using a general physical constraint, which quantifies how each basis material in the object is mixed together to form the object, within the series of equations, wherein the general physical constraint is determined using at least one of (i) the equations and a multi-energy CT measurement to solve unknown parameters in the general physical constraint, together with solving mass densities of each basis material or (ii) reference data of predetermined parameters, which are based on existing data or empirical measurements that are independent of multi-energy CT measurements. The method also includes determining at least one basis material density of the object using the physical constraint and the CT imaging data and generating an image of the object using the CT imaging data and the mass densities of at least one basis material.

In one configuration, a computed tomography (CT) imaging system is provided that includes at least one x-ray source configured to emit x-rays at a plurality of energy levels toward an object to be imaged and at least one detector configured to receive x-rays that are attenuated by the object. The system also includes a data acquisition system (DAS) connected to the at least one detector to receive an indication of received x-rays at the plurality of energy levels and a computer system coupled to the DAS to receive the indication of the received x-rays at the plurality of energy levels. The computer system is programmed to acquire CT imaging data corresponding to each of at least two different energy spectral bins or spectra and use the CT imaging data at each of the last least two different energy spectral bins or spectra to form a series of equations for basis material decomposition. The computer system is also programmed to use a general physical constraint, which quantifies how each basis material in the object is mixed together to form the object, within the series of equations, wherein the general physical constraint is determined using at least one of (i) the equations and a multi-energy CT measurement to solve unknown parameters in the general physical constraint, together with solving mass densities of each basis material or (ii) reference data of predetermined parameters, which are based on existing data or empirical measurements that are independent of multi-energy CT measurements. The computer system is further programmed to determine at least one basis material density of the object using the physical constraint and the CT imaging data and generate an image of the object using the CT imaging data and the mass densities of at least one basis material.

Various other features of the present invention will be made apparent from the following detailed description and the drawings.

DETAILED DESCRIPTION

Figure 1A:
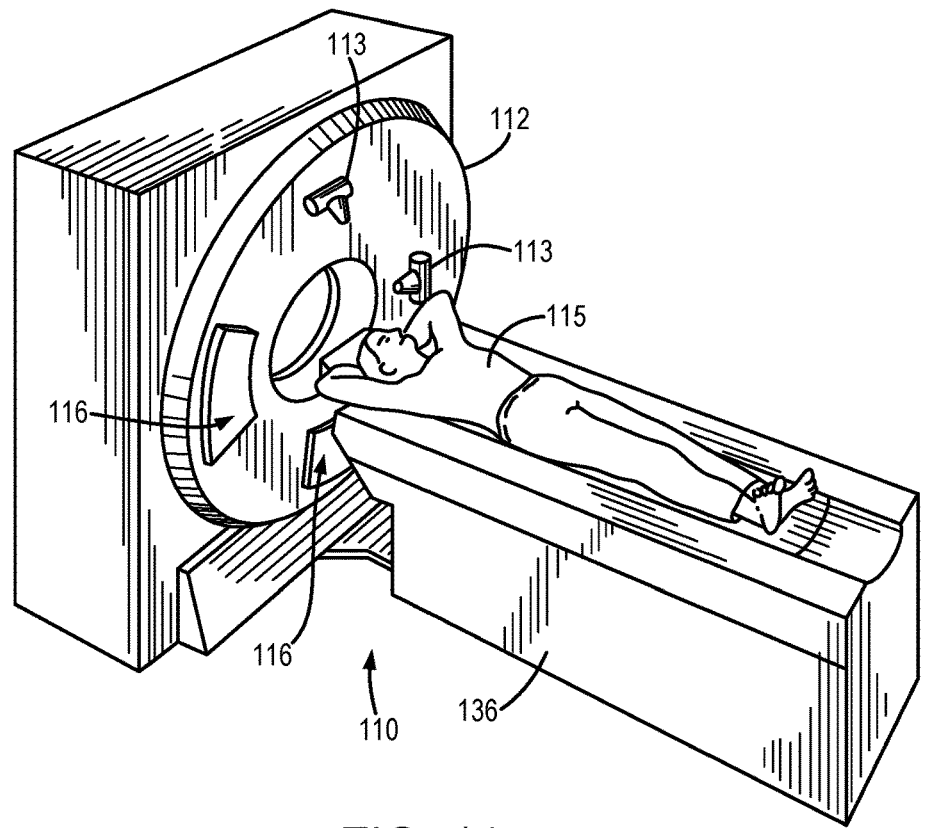
FIG. 1A is a CT imaging system in which the present invention may be employed.

Multi-energy CT (MECT) has gained increasing interest in clinical medicine and can be performed using both multi-source and single-source CT systems. Within the general category of MECT, some particular clinical applications have gained substantial acceptance. For example, quantitative basis material density maps, which can be generated with MECT, can be used to aid clinical diagnosis and treatment, such as iodine quantification and liver iron quantification. Electron density maps generated with MECT can also be used for radiation treatment planning. Basis materials may include water, and the like, or contrast agents, such as iodine, bismuth, gadolinium, and the like.

In addition, secondary images can be generated from post-processing of material decomposition results for various clinical applications. For instance, virtual non-contrast, virtual monochromatic, and virtual monoenergetic images can be generated and used for clinical applications including bone removal, measuring stone composition, gout imaging, and liver fat quantification.

A number of material decomposition methods are known. These methods can be categorized as projection-based, image-based, or combined methods. Projection-based methods are primarily limited by the lack of availability of projection data in routine clinical practice. Image-based methods work directly on reconstructed images and therefore may be more convenient for clinical environments. As stated above, in DECT, material decomposition methods frequently assume volume conservation, allowing three basis materials to be decomposed from two energy measurements. Volume conservation is based on the assumption that the sum of the volumes of each basis material is equal to the volume of the mixture, which means that any volume of one material is to replace the same volume of other materials in a mixture. In MECT with more than two energy bins (e.g., energy resolved photon-counting CT), although the number of energy measurements is sufficient to solve more than two basis materials, additional constraints such as volume conservation are still beneficial to be included to improve noise properties. However, volume conservation is often violated in solutions or mixtures. Errors in presumed volume conservation could lead to bias in material quantification.

As will be described in further detail, the present disclosure provides improvement in material decomposition methods by introducing a general physical constraint in the material decomposition without assuming volume conservation. This general physical constraint of material mixture is applicable to material decomposition methods in projection domain, image domain, or both.

Thus, as will be described, the systems and methods provided herein introduce a general physical constraint in the material decomposition process without assuming the total volume is conserved. The general physical constraint may include an unknown parameter. The unknown parameter in the general physical constraint can be determined using multi-energy measurement data, or using calibration measurement data, which can be measured on the mixture density, or can be calibration data obtained from previous measurements (e.g., using reference data, which may be reference data from existing literature). In this way, one can improve the quantitative accuracy of the material density decomposition, as well as the noise performance of the material decomposition.

In some embodiments, the general physical constraint may be represented as a variable. The variable may be determined from multi-energy measurements. Additionally, in some embodiments, the variable may be predetermined from a lookup table of reference data or be expressed as a function of basis material densities.

In some embodiments, calibration data, such as reference data, can be provided. The reference data may be arranged as a lookup table or a function of basis material densities, and may be created based on published values relating to material composition or measured information (e.g., based on experimental data from separate data acquisitions from the object). The general physical constraint of basis materials in the mixture is a condition that does not need to be dependent on X-ray CT measurements. For example, formulations (such as weighting and measuring) and well-calibrated devices can provide suitable accuracy for the acquisition of reference data. Additionally, published data on basis material composition and densities in their mixture can be used to create the reference data. Other analytical instruments or techniques capable of material composition analysis and quantification can also be used to generate the reference data.

Figure 1B:
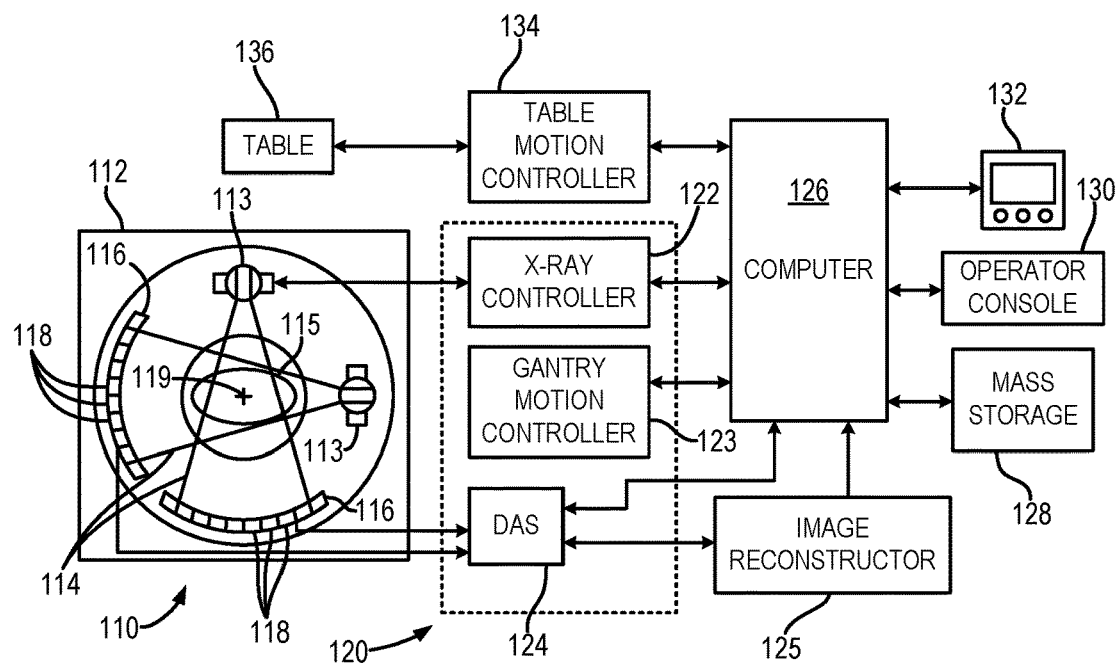
FIG. 1B is a block schematic diagram of the CT imaging system of FIG. 1A.

With initial reference to FIGS. 1A and 1B, a computed tomography (CT) imaging system 110 includes a gantry 112 representative of at least a "multi-energy" CT system. In the illustrated example, the gantry 112 has a pair of x-ray sources 113 that each projects a respective fan beam or cone beam of x-rays 114 toward a detector array 116 on the opposite side of the gantry 112. Such illustration of a "dual source" system is non-limiting. For example, the systems and methods of the present invention may likewise be used with traditional "single source" CT systems that are controlled to effectuate a multi-energy imaging process. The detector array 116 may include traditional, "energy integrating" detectors or may include "photon counting" and/or "energy discriminating" detectors. In any case, the detector array 116 is formed by a number of detector elements 118 that together sense the projected x-rays that pass through a medical patient or subject 115. During a scan to acquire x-ray projection data, the gantry 112 and the components mounted thereon rotate about a center of rotation 119 located within the subject 115 to acquire CT data.

The rotation of the gantry 112 and the operation of the x-ray source(s) 113 are governed by a control mechanism 120 of the CT system 110. The control mechanism 120 includes an x-ray controller 122 that provides power and timing signals to the x-ray source(s) 113 and a gantry motor controller 123 that controls the rotational speed and position of the gantry 112. A data acquisition system (DAS) 124 in the control mechanism 120 samples analog data from detector elements 118 and converts the data to digital signals for subsequent processing. An image reconstructor 125, receives sampled and digitized x-ray data from the DAS 124 and performs high speed image reconstruction. The reconstructed image is applied as an input to a computer 126 that stores the image in a mass storage device 128.

The computer 126 also receives commands and scanning parameters from an operator via, for example, console 130. An associated display 132 allows the operator to observe the reconstructed image and other data from the computer 126. The operator-supplied commands and parameters are used by the computer 126 to provide control signals and information to the DAS 124, the x-ray controller 122, and the gantry motor controller 123. In addition, the computer 126 can operate a table motor controller 134 that controls a motorized table 136 to position the patient 115 in the gantry 112.

Turning to the material decomposition process, below an image-based material decomposition algorithm is used as an example to describe how the general physical constraint is used in the material decomposition process. It should be noted that this constraint can also be used in projection-based or combined methods for material decomposition. An image-based material decomposition method can be implemented on either linear attenuation coefficient or CT number in Hounsfield unit (HU).

The x-ray attenuation when passing through a medium is dependent on the mass attenuation coefficient (MAC), which is energy dependent, and the mass density of the medium. The linear attenuation coefficient (LAC), μ, of a mixture composed of M basis materials at an x-ray energy, E, can be expressed as, $$\mu(E) = \sum_{i=1}^{M} \left(\frac{\mu}{\rho}\right)_i (E) \cdot \rho_i$$

where $(\mu/\rho)$ (E) and $\rho_i$ are MAC and mass density of the ith material in the mixture, respectively.

An example of an image-based material decomposition method can be described by the following linear equation system:

$$\begin{cases} \mu(E_1) = \sum_{i=1}^{M} \left(\frac{\mu}{\rho}\right)_i (E_1) \cdot \rho_i \\ \mu(E_2) = \sum_{i=1}^{M} \left(\frac{\mu}{\rho}\right)_i (E_2) \cdot \rho_i \\ \quad \vdots \\ \mu(E_N) = \sum_{i=1}^{M} \left(\frac{\mu}{\rho}\right)_i (E_N) \cdot \rho_i \\ 1 = \sum_{i=1}^{M} \frac{\rho_i}{\rho_{i0}} (\text{prior}) \end{cases} \xrightarrow{\text{matrix form}}$$

$$[\vec{\mu}]_{N \times 1} = [A]_{N \times M} [\vec{\rho}]_{M \times 1} \text{ without prior}$$

or $$\begin{bmatrix} \vec{\mu} \\ 1 \end{bmatrix}_{(N+1) \times 1} = \begin{bmatrix} A \\ 1/\rho_0 \end{bmatrix}_{(N+1) \times M} [\vec{\rho}]_{M \times 1} \text{ with prior}$$

where $$\vec{\mu} = \begin{bmatrix} \mu(E_1) \\ \vdots \\ \mu(E_N) \end{bmatrix}$$

$$\vec{\rho} = \begin{pmatrix} \rho_1 \\ \vdots \\ \rho_M \end{pmatrix}$$

$$1/\rho_0 = (1/\rho_{10} \ldots 1/\rho_{M0}); \text{ and}$$

$$A = \begin{bmatrix} \left(\frac{\mu}{\rho}\right)_1(E_1) & \left(\frac{\mu}{\rho}\right)_2(E_1) & \cdots & \left(\frac{\mu}{\rho}\right)_M(E_1) \\ \vdots & \ddots & & \vdots \\ \left(\frac{\mu}{\rho}\right)_1(E_N) & \left(\frac{\mu}{\rho}\right)_2(E_N) & \cdots & \left(\frac{\mu}{\rho}\right)_M(E_1) \end{bmatrix}.$$

Here, N is the number of x-ray beam measurements (i.e., N=2 for DECT and N≥3 for MECT), M is the number of basis materials, μ(E) is the effective LAC from the x-ray beam measurements, and (μ/ρ)(E) is the effective MAC, which may be determined by a separate calibration procedure. The last row in Eqn. (2), $$1 = \sum_{i=1}^{M} (\rho_i / \rho_{i0})$$

refers to volume conservation (prior information) defined for materials i=1,2,..., M, where $\rho_i$ and $\rho_{i0}$ are the mass density of the ith basis material in the mixture and its pure form. When the linear equation system is overdetermined, it can be solved using an ordinary least squares optimization method.

The MAC of compounds or mixtures can thus be expressed as, $$\frac{\mu}{\rho} = \sum_{i=1}^{N} w_i \left(\frac{\mu}{\rho}\right)_i \qquad (1)$$

where $$\left(\frac{\mu}{\rho}\right)$$

is the MAC of the mixture, $$\left(\frac{\mu}{\rho}\right)_i$$

and $w_i$ are the MAC and mass fraction of basis material i.

In some instances, LAC values can be converted to CT number values (e.g., Hounsfield units). According to the present disclosure, the CT number may be used directly. The relationship between CT number and LAC may be expressed as, $$CT = \frac{\mu - \mu_w}{\mu_w} \times 1000 \qquad (2)$$

Combining Equations (1) and (2), a system of equations for multi-energy CT measurements may be derived as, $$CT(E) = CT(E)_1 \frac{\hat{\rho}_1}{\rho_1} + CT(E)_2 \frac{\hat{\rho}_2}{\rho_2} + \ldots + CT(E)_N \frac{\hat{\rho}_N}{\rho_N} + 1000(\delta - 1) \qquad (3)$$

a general condition on physical constraint in the mixture may be used:

$$\delta = \frac{\hat{\rho}_1}{\rho_1} + \frac{\hat{\rho}_2}{\rho_2} + \ldots + \frac{\hat{\rho}_N}{\rho_N} = \frac{V_1}{\hat{V}} + \frac{V_2}{\hat{V}} + \ldots + \frac{V_N}{\hat{V}} \qquad (4)$$

where $\hat{\rho}_i$ is the density (or concentration) of the ith basis material in the mixture and $\rho_i$ is its density in its pure form. $V_i$ is the volume of the ith basis material in its pure form and $\hat{V}$ is the volume of the mixture. $CT(E)_i$ represents the CT number of the ith basis material in its pure form at energy E. Here, δ depends on the composition of basis materials. δ may be smaller or larger than 1.

A value of δ=1 represents volume conservation. In one non-limiting example, δ>1 for a mixture of calcium chloride ($CaCl_2$) and water, which has a decreased volume relative to the sum of the individual component volumes. In another non-limiting example, δ<1 for a biopolymer-water solution, which has a total volume that is greater than the sum of the individual component volumes.

Equations (3) and (4) may be further rearranged into the following matrix form:

$$\begin{bmatrix} CT(E_1) \\ \vdots \\ CT(E_M) \\ 1000 \end{bmatrix} = \begin{bmatrix} CT(E_1)_1/\rho_1 & \vdots & CT(E_1)_N/\rho_N & 1000 \\ \vdots & \vdots & \vdots & \vdots \\ CT(E_M)_1/\rho_1 & \vdots & CT(E_M)_N/\rho_N & 1000 \\ 1000/\rho_1 & \vdots & 1000/\rho_N & -1000 \end{bmatrix} \begin{bmatrix} \hat{\rho}_1 \\ \vdots \\ \hat{\rho}_N \\ \delta - 1 \end{bmatrix} \qquad (5)$$

Here, δ−1 represents the percent change of volume due to mixing, a metric that evaluates the violation of volume conservation. Equation (5) may be rearranged into the following form:

$$\begin{bmatrix} CT(E_1) \\ \vdots \\ CT(E_M) \\ 1000 \end{bmatrix} - \begin{bmatrix} 1000(\delta-1) \\ \vdots \\ 1000(\delta-1) \\ -1000(\delta-1) \end{bmatrix} = \begin{bmatrix} CT(E_1)_1/\rho_1 & \vdots & CT(E_1)_N/\rho_N \\ \vdots & \vdots & \vdots \\ CT(E_M)_1/\rho_1 & \vdots & CT(E_M)_N/\rho_N \\ 1000/\rho_1 & \vdots & 1000/\rho_N \end{bmatrix} \begin{bmatrix} \hat{\rho}_1 \\ \vdots \\ \hat{\rho}_N \end{bmatrix} \qquad (6)$$

When the second term in Equation (6) is equal to zero, it is equal to a method with a volume conservation constraint:

$$\begin{bmatrix} CT(E_1) \\ \vdots \\ CT(E_M) \\ 1000 \end{bmatrix} = \begin{bmatrix} CT(E_1)_1/\rho_1 & \vdots & CT(E_1)_N/\rho_N \\ \vdots & \vdots & \vdots \\ CT(E_M)_1/\rho_1 & \vdots & CT(E_M)_N/\rho_N \\ 1000/\rho_1 & \vdots & 1000/\rho_N \end{bmatrix} \begin{bmatrix} \hat{\rho}_1 \\ \vdots \\ \hat{\rho}_N \end{bmatrix} \qquad (7)$$

When the volume is not conserved, the second term in Equation (6) is nonzero. Accordingly, applying material decomposition (Equation (7)) with a volume conservation constraint can result in bias in the estimation of basis material densities.

In one non-limiting example, where $CT(E)_{i0}$, i=I, Gd, and W denote the CT number of basis materials iodine (I), gadolinium (Gd), and water (W) in their pure forms at X-ray beam energy E, the term $$\frac{CT(E)_W}{\rho_{W0}}\rho_W$$

is dropped since in theory $$\frac{CT(E)_W}{\rho_{W0}} = 0,$$

and the last term, $1000 \cdot (\delta-1)$, can be treated in three conditions:
1) $1000 \cdot (\delta-1) \neq$ Constant: when this term is treated as a variable, another unknown is introduced and needs to be calibrated;
2) $1000-(\delta-1)=$Constant$\neq 0$: when the term is treated as a nonzero constant, another physical constraint that is not exactly the volume conservation has been already incorporated;
3) $1000-(\delta-1)=$Constant$=0$: when the term is treated as zero, volume conservation is applied because $\delta=1$.

According to one embodiment in accordance with the present disclosure, a method of incorporating the general physical constraint parameter $\delta$ (Equation (5)) is described. The general physical constraint may be considered as an unknown variable. In one non-limiting embodiment, the unknown variable may be solved using the multi-energy measurements.

According to another embodiment in accordance with the present disclosure, a method of incorporating the general physical constraint parameter $\delta$ (Equation (5)) is described. The general physical constraint may be considered as either an unknown variable that is to be solved together with material density using multiple energy measurement or a predetermined parameter based on reference data. In one non-limiting embodiment, reference data may be used to determine basis material densities. The reference data may be used in the form of a lookup table, and may be created based on material properties. The material properties may include, but are not limited to, the physical density of mixture components. The reference data may be stored in a memory associated with the CT imaging system.

As stated above, in some embodiments the reference data may be obtained from published values. In other embodiments, the reference data may be obtained from separate measurements. The separate measurements may come from the same object, or may be calculated from a plurality of objects.

Using reference data to determine basis material densities can provide unique benefits. In some situations, using reference data may reduce the bias in the material decomposition. Specifically, bias may be reduced when compared to methods that assume volume conservation.

Additionally, using reference data may result in an improved noise property and/or image artifacts in material decomposition. In some situations, an improvement in noise property may occur when compared to methods using an unknown variable to represent the general physical constraint.

Once the general physical constraint parameter $\delta$ of each basis component in the mixture has been determined, the basis material concentration may be solved using an inversion equation:

$$[\hat{\rho}]=[M]^{-1}[CT] \quad (8)$$

where vector $\hat{\rho}$ is the unknown basis material densities, M is a material matrix associated with the attenuation properties of the basis materials, and [CT] is the vector of CT numbers measured at multiple energies shown in the left side of Eq. 6.

In some embodiments, an iterative method may be used to solve the material concentration. As will be described, a physical constraint, which in a non-limiting example may be a constraint on volume changes or constraint on basis material density, or the like, may be used to solve the material concentration. As will also be described, the systems and methods described herein can be applied with image-based, projection-based, and combined techniques.

In some embodiments, a Figure of Merit (FOM) may be determined to quantify the overall noise magnification of a material decomposition process, which is given by $$\frac{\|\delta\vec{\rho}\|}{\|\vec{\rho}\|},$$

the overall relative noise in the solution to the linear equation system. Suppose the measurement noise is given by $\delta\vec{\mu}$ and the corresponding noise in the solution ($\vec{\rho}$) of the linear system is $\delta\vec{\rho}$, according to the definition of the condition number for a linear equation system, the upper bound of the relative noise, $$\frac{\|\delta\vec{\rho}\|}{\|\vec{\rho}\|}$$

is given by $$\frac{\|\delta\vec{\rho}\|}{\|\vec{\rho}\|} \leq \begin{cases} cond(A)\frac{\|\delta\vec{\mu}\|}{\|\vec{\mu}\|} & \text{without prior} \\ cond\begin{pmatrix} A \\ 1/\rho_0 \end{pmatrix}\frac{\|\delta\vec{\mu}\|}{\left\|\begin{pmatrix}\vec{\mu}\\1\end{pmatrix}\right\|} & \text{with prior} \end{cases}, \quad (9)$$

where cond(•) and ‖•‖ denote the condition number of a matrix and the norm of a vector, respectively. For the same measurement noise, $\delta\vec{\mu}$, this upper bound serves as a single FOM to represent the overall noise magnification in the material decomposition, such as an image-based material decomposition, process with/without incorporating the prior information. Prior information may be volume conservation data, or reference data, which may be a priori data and/or may be acquired from the subject or maintained as a database or look-up table. Incorporating prior information, such as volume conservation, into the material decomposition process may improve the noise performances without significantly sacrificing the quantification accuracy.

In some embodiments, bias may be assessed due to inaccurate prior information. The prior information such as volume conservation may not be accurate, especially for those contrast materials in solution format. A small error of the prior information may be propagated into the solution. Assuming that the total volume of a mixture is not strictly conserved (i.e., the total volume does not equal the summation of the volume of each material), the error term is given by $$1 + \delta = \sum_{i=1}^{M} \frac{\rho_{\delta i}}{\rho_{i0}} \qquad (10)$$

Applying Eq. (10), one can derive $$\begin{bmatrix} \vec{\mu} \\ 1 + \delta \end{bmatrix} = \begin{bmatrix} A \\ 1/\rho_0 \end{bmatrix} \vec{\rho_\delta} \qquad (11)$$

Mass densities, $\vec{\rho}$ and $\vec{\rho_\delta}$ can be solved as $$\begin{cases} \vec{\rho} = \begin{bmatrix} A \\ 1/\rho_0 \end{bmatrix}^\dagger \begin{bmatrix} \vec{\mu} \\ 1 \end{bmatrix} = \left\{ \begin{bmatrix} A \\ 1/\rho_0 \end{bmatrix}^T \begin{bmatrix} A \\ 1/\rho_0 \end{bmatrix} \right\}^{-1} \begin{bmatrix} A \\ 1/\rho_0 \end{bmatrix}^T \begin{bmatrix} \vec{\mu} \\ 1 \end{bmatrix} \\ \vec{\rho_\delta} = \begin{bmatrix} A \\ 1/\rho_0 \end{bmatrix}^\dagger \begin{bmatrix} \vec{\mu} \\ 1 + \delta \end{bmatrix} = \left\{ \begin{bmatrix} A \\ 1/\rho_0 \end{bmatrix}^T \begin{bmatrix} A \\ 1/\rho_0 \end{bmatrix} \right\}^{-1} \begin{bmatrix} A \\ 1/\rho_0 \end{bmatrix}^T \begin{bmatrix} \vec{\mu} \\ 1 + \delta \end{bmatrix} \end{cases} \qquad (12)$$

where $[\bullet]^\dagger$ denotes the pseudoinverse and $[\bullet]^\dagger = \{[\bullet]^T[\bullet]^{-1}\} [\bullet]^T$. Then the difference between $\vec{\rho}$ and $\vec{\rho_\delta}$ is given by $$\vec{\rho_\delta} - \vec{\rho} = \left\{ \begin{bmatrix} A \\ 1/\rho_0 \end{bmatrix}^T \begin{bmatrix} A \\ 1/\rho_0 \end{bmatrix} \right\}^{-1} \begin{bmatrix} A \\ 1/\rho_0 \end{bmatrix}^T \left\{ \begin{bmatrix} \vec{\mu} \\ 1 + \delta \end{bmatrix} - \begin{bmatrix} \vec{\mu} \\ 1 \end{bmatrix} \right\} = \qquad (13)$$

$$\left\{ \begin{bmatrix} A \\ 1/\rho_0 \end{bmatrix}^T \begin{bmatrix} A \\ 1/\rho_0 \end{bmatrix} \right\}^{-1} \begin{bmatrix} A \\ 1/\rho_0 \end{bmatrix}^T \begin{bmatrix} \vec{0} \\ \delta \end{bmatrix} = B \begin{bmatrix} \vec{0} \\ \delta \end{bmatrix} = \delta \begin{pmatrix} b_{1,N+1} \\ b_{2,N+1} \\ \vdots \\ b_{M,N+1} \end{pmatrix}$$

where $$\left\{ \begin{bmatrix} A \\ 1/\rho_0 \end{bmatrix}^T \begin{bmatrix} A \\ 1/\rho_0 \end{bmatrix} \right\}^{-1} \begin{bmatrix} A \\ 1/\rho_0 \end{bmatrix}^T$$

is written as a new matrix B and $$\begin{pmatrix} b_{1,N+1} \\ b_{2,N+1} \\ \vdots \\ b_{M,N+1} \end{pmatrix}$$

denotes the last column in matrix B. Thus $\delta b_{1,N+1}$, $\delta b_{2,N+1}$, ..., $\delta b_{M,N+1}$ represent the biases of mass densities for $\rho_1, \rho_2, \ldots, \rho_M$ when an error term $\delta$ is introduced.

Figure 2:
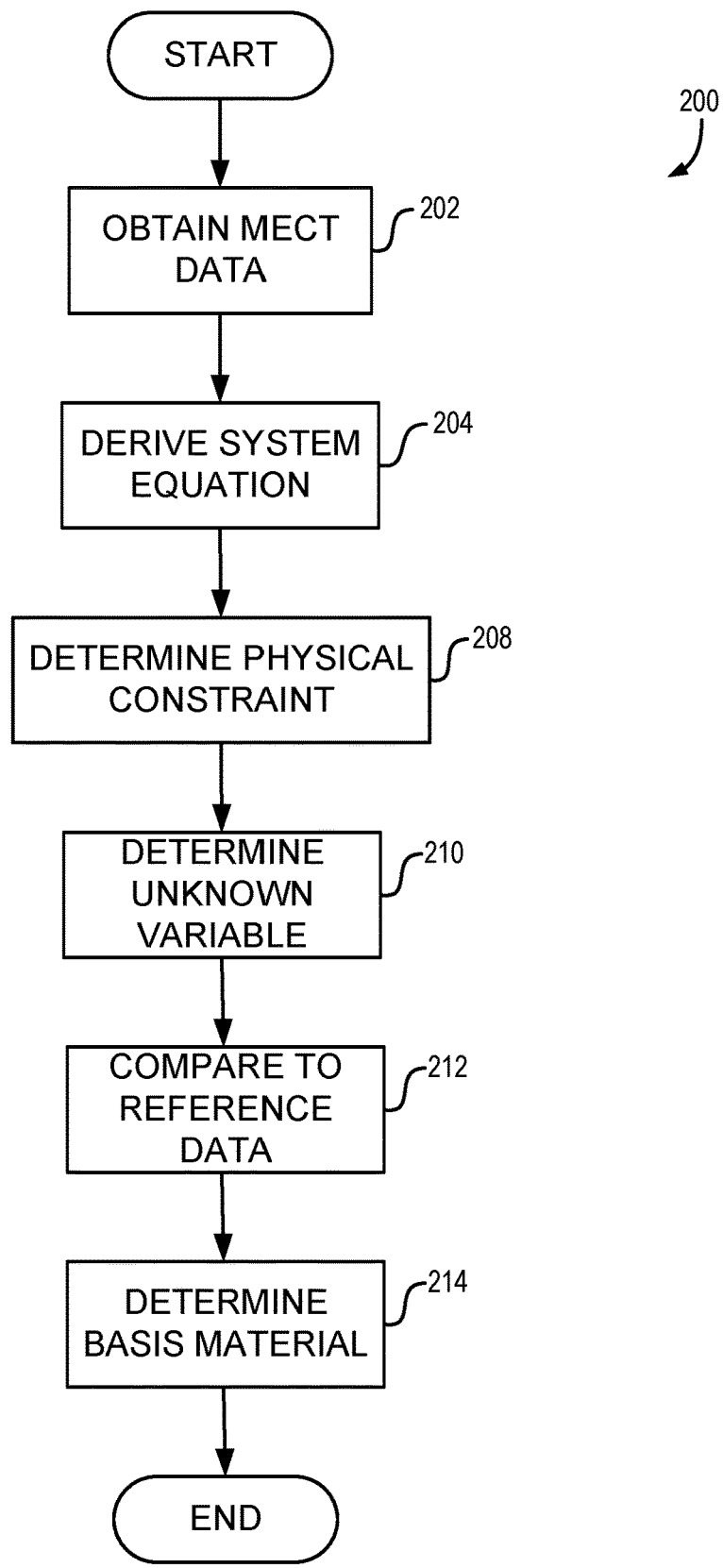
FIG. 2 is a flow chart setting forth some non-limiting examples of steps of processes for achieving material decomposition for MECT images.

Referring to FIG. 2, a process 200 in accordance with the present disclosure includes obtaining MECT data at process block 202. This may include performing an imaging process using a CT system, such as described above with respect to FIGS. 1A and 1B, or simply accessing stored MECT data. Once the MECT data is acquired at process block 202, the MECT data 202 may be used to derive a system equation for multi-energy CT measurement at process block 204. Once the system equation is derived, a physical constraint may be determined at process block 208. The physical constraint may or may not relate to volume conservation but may be assigned to an unknown variable at process block 210. Then, the unknown variable may be compared to reference data at process block 212. The reference data, as described, may be a priori data and/or may be acquired from the subject or maintained as a database or look-up table. After the comparison, at least one basis material may be determined via the reference data at process block 214. The basis materials can be visually depicted by generating basis material maps that indicate the spatial distribution of the relevant basis material in the imaging volume.

Figure 3:
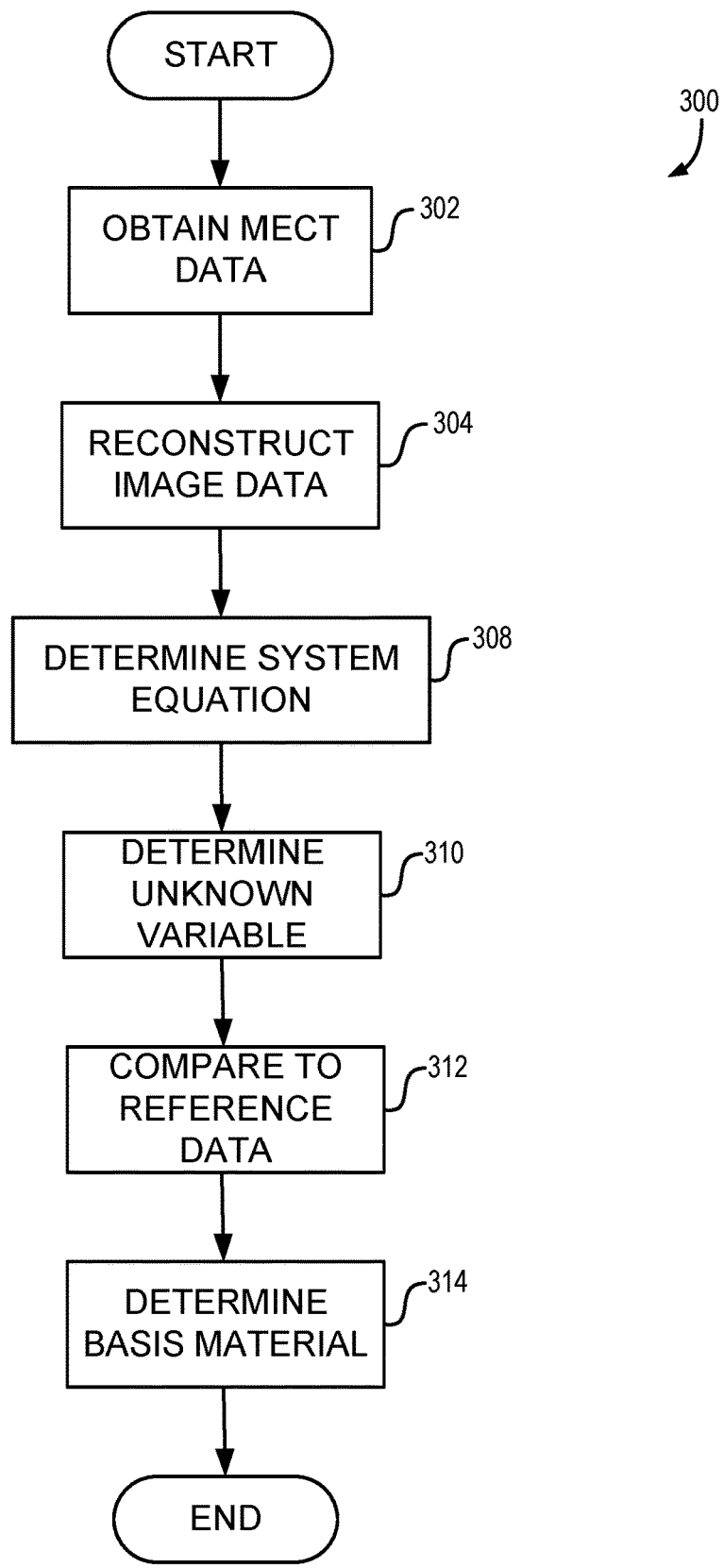
FIG. 3 is another flow chart setting forth some non-limiting examples of steps of processes for achieving material decomposition for MECT images.

Referring to FIG. 3, a process 300 in accordance with the present disclosure includes obtaining MECT data at process block 302. Again, this may include performing an imaging process using a CT system, such as described above with respect to FIGS. 1A and 1B, or simply accessing stored MECT data. Once the MECT data is acquired at process block 302, the MECT data 302 may be reconstructed to produce image data associated with each of the energy levels at process block 304. Using the image data, a system equation may be determined at process block 308. Then, an unknown variable associated with a volume conservation constraint may be determined at process block 310. The unknown variable may be compared to reference data at process block 312. Again, the reference data, as described, may be a priori data and/or may be acquired from the subject or maintained as a database or look-up table. At least one basis material may then be determined from reference data at process block 314. The basis materials can be visually depicted by generating basis material maps that indicate the spatial distribution of the relevant basis material in the imaging volume.

Figure 4:
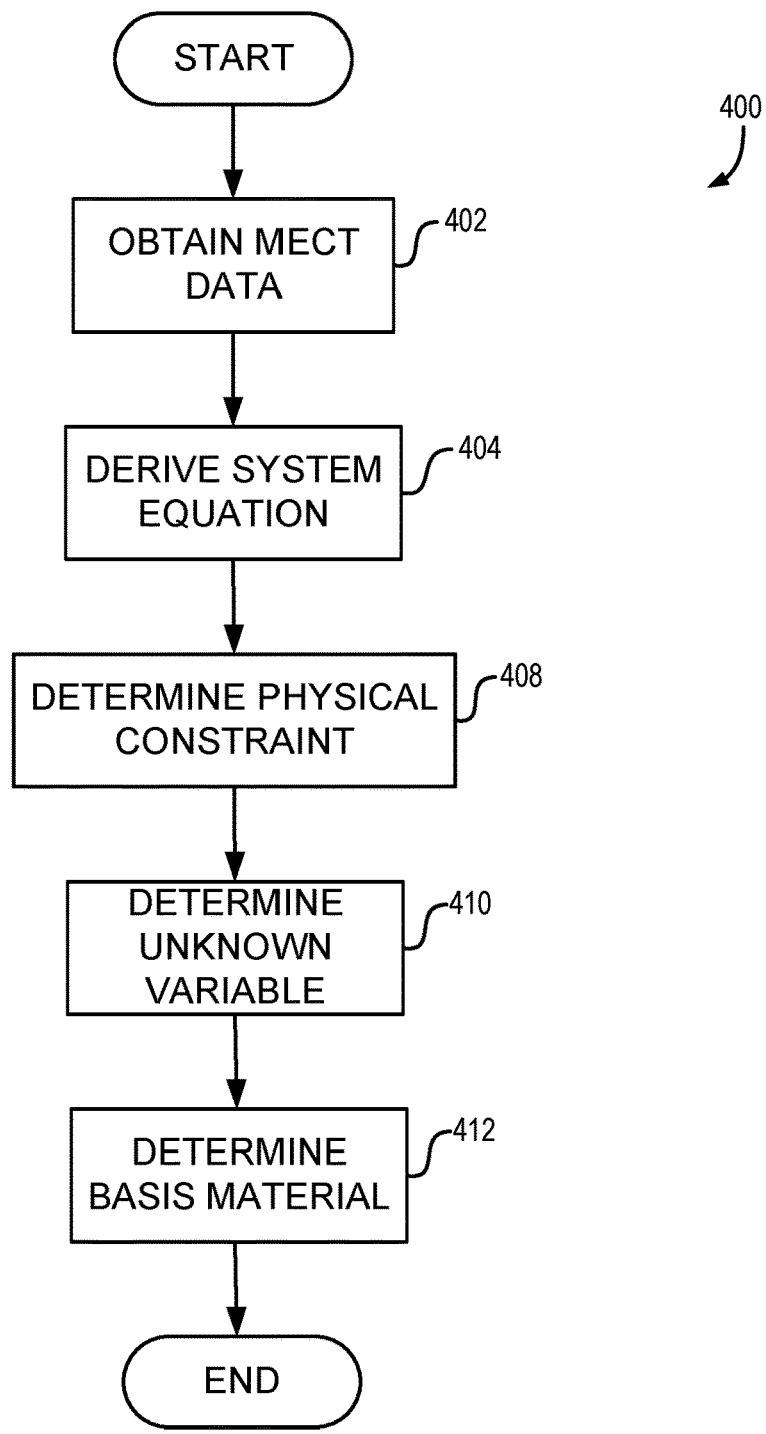
FIG. 4 is another flow chart setting forth some non-limiting examples of steps of processes for achieving material decomposition for MECT images.

Referring to FIG. 4, a process 400 in accordance with the present disclosure includes obtaining MECT data at process block 402. This may include performing an imaging process using a CT system, such as described above with respect to FIGS. 1A and 1B, or simply accessing stored MECT data. Once the MECT data is acquired at process block 402, the MECT data 402 may be used to derive a system equation for multi-energy CT measurement at process block 404. Once the system equation is derived, a volume conservation constraint may be determined at process block 408. The volume conservation constraint may be assigned to an unknown variable at process block 410. Then, the unknown variable may be used to determine at least one basis material via multi-energy measurements at process block 412, such as by solving the equations. To this end, the solving may be performed without reference data, as described.

Example Two-Material and Three-Material Decompositions

In one non-limiting example, two cylindrical water phantoms with a diameter of 20 cm were designed for two-material decomposition (iodine and water) and three-material decomposition (iodine, gadolinium, and water) tasks, respectively. Each phantom contained nine different contrast material samples. The two phantoms and the 9 contrast material samples with material types and concentrations were labelled. A calibration procedure to determine the coefficients in the decomposition matrix was performed on another water phantom with an identical diameter, but with contrast samples with different concentrations and at different locations.

Three CT scan configurations were simulated in this study: DECT, MECT (N=3), and PCD-CT (N=4). The spectra for DECT were generated based on a dual-source dual-energy CT (DS-DECT) scan configuration with a tube potential configuration of 80/Sn140 kV (Sn: 0.4 mm). The spectra for MECT (N=3) were represented by three energy beams, one low energy beam and two high energy beams. The low energy spectrum was identical to the 80 kV beam in the DECT simulation, while the two high energy beams were generated based on a "Twin Beam" design through adding a split filter (0.4 mm Sn and 0.12 mm Au) on the 140 kV beam. The spectra for PCD-CT (N=4) were generated by simulating four energy bins in a PCD-CT with threshold settings of [25 50 75 90 keV] at 140 kV.

The two-material phantom was used for DECT simulation, with and without the prior information to study the impact of the prior information on DECT. The three-material phantom was for MECT (N=3) and PCD-CT (N=4), with and without the prior information. Since DECT with prior can also solve the three-material problem, it was included as a reference. All images were reconstructed with a filtered-backprojection algorithm with a Hamming smooth window. The information about data acquisition geometry, radiation dose and material decomposition for two and three-material phantom scans is summarized in Table 1.

with the same threshold settings of ([25 50 75 90 keV]) as in the simulation study. Images were reconstructed using a quantitative convolutional kernel (D30f). The information about data acquisition geometry, radiation dose and material decomposition for two and three-material phantom scans is summarized in Table 2.

TABLE 2

Data acquisition geometry, radiation dose, and material decomposition in the experimental study

|  | 2-Material | 3-Material |
|---|---|---|
| CT Scanner Platform | DECT | PCD-CT (N = 4) |
| Phantom Size (cm) | 32 × 25 | 25 × 18.5 |
| kV | 80/Sn140 | 140: [25 50 75 90 keV] |
| Mean Energies (keV) | [52.2 88.8] | [64.6 69.5 88.7 108.7] |
| Focal Length (mm) |  | 595 |
| Source Detector Distance (mm) |  | 1095.6 |
| Detector Shape/Type/Material/ | Cylindrical/EID*/Gd$_2$O$_2$S | Cylindrical/PCD/CdTe |
| Collimation (mm) | 64 × 0.6 | 32 × 0.5 |
| # of channels/projections/rows | 736/1152/64 | 480/1152/32 [40] |
| Slice-thickness/Increment (mm) |  | 3.0/2.8 |
| Recon Kernel | Q30 | D30 |
| CTDIvol (mGy) | 8.17 | 35.34 |
| Material Decomposition | With and without prior | With and without prior |

Table 3 provides the quantification bias of the mass density for iodine in two-material decomposition using 21

TABLE 1

Data acquisition geometry, radiation dose, and material decomposition in the simulation study.

|  | 2-Material | 3-Material | | |
|---|---|---|---|---|
| CT Scanner Platform | DECT | DECT | MECT (N = 3) | PCD-CT (N = 4) |
| kV | 80/Sn140 | 80/Sn140 | 80/Au140/Sn140 | 140: [25 50 75 90 keV] |
| Mean Energies (keV) | [52.2 88.8 ] | [52.2 88.8 ] | [52.2 75.4 88.8 ] | [62.6 68.8 88.3 108.3] |
| Focal Length (mm) |  |  | 595 |  |
| Source Detector Distance (mm) |  |  | 1095.6 |  |
| Detector Shape/Type/Material/ |  | Cylindrical/EID*/Gd$_2$O$_2$S |  | Cylindrical/PCD/CdTe |
| # of channels/projections/rows |  |  | 736/1152/1 |  |
| Slice Width (mm) |  |  | 0.6 |  |
| CTDIvol (mGy) | 16.40 | 16.40 | 16.67 | 16.40 |
| Material Decomposition | With and without prior | With prior (used as a reference) | With and without prior | With and without prior |

*EID = energy integrating detector

Two-material decomposition was first performed using a phantom containing two basis materials of water and iodine, with and without the prior information to study the impact of the prior information on DECT. CT data were collected using a second generation DS-DECT (Somatom Definition Flash, Siemens Healthcare) with a voltage pair of 80/Sn140 kV. Images were reconstructed using a quantitative convolutional kernel (Q30f).

In one non-limiting example, a water filled phantom inserted with three iodine, three gadolinium, and two mixtures was prepared for three-material decomposition, with and without the prior information. The three-material phantom was scanned with a whole-body research PCD-CT scanner prototype (Somatom CounT, Siemens Healthcare)

consecutive slices, and that for iodine and gadolinium in three-material decomposition using 11 consecutive slices. No bias for iodine quantification is observed in two-material decomposition without the prior. In contrast, a small bias of 0.03±0.02 mg/cc is calculated with the prior, due to the violation of the assumption for volume conservation. In three-material decomposition, the averaged biases for iodine and gadolinium quantifications are 0.30±0.18 mg/cc and −0.10±0.08 mg/cc without the prior, and are 0.20±0.12 mg/cc and −0.04±0.04 mg/cc with the prior. The biases calculated without the prior may be caused by the cross-contamination between two contrast materials, while those with the prior may be due to both cross-contamination and violation of the assumption for volume conservation.

TABLE 3

Summary of bias in iodine/gadolinium quantification
in experiments (unit: mg/cc)

|  | 2-Material | 3-Material |
|---|---|---|
| CT Scanner Platform | DECT | PCD-CT |
| Iodine w/o prior | 0.00 ± 0.03 | 0.30 ± 0.18 |
| Iodine w/prior | 0.03 ± 0.02 | 0.20 ± 0.12 |
| Gadolinium w/o prior | N/A | −0.10 ± 0.08 |
| Gadolinium w/prior |  | −0.04 ± 0.04 |

The difference ($\vec{\rho}_\delta - \vec{\rho}$) between mass densities with and without introducing the error term δ can be plotted as a function of δ. The value of δ corresponding to an averaged bias of 0.03 mg/cc in two-material decomposition is −0.001, implying an averaged violation of volume conservation of about 0.1% for given iodine mass densities (7.5 mg/cc). Similarly, the values of δ to averaged biases of 0.20 mg/cc (iodine) and −0.04 mg/cc (gadolinium) in three-material decomposition are 0.004 and 0.001, implying violations of volume conservation of about 0.4% and 0.1% for given iodine mass densities (≤15.0 mg/cc) and gadolinium mass density (≤10.2 mg/cc), respectively.

The average noise level in the water map was significantly reduced when the prior information (volume conservation) was incorporated into the material decomposition process. This can be explained as follows. Considering three-material decomposition of iodine, gadolinium, and water in, $\rho_W$ and $\text{Var}(\rho_W)$ can be described as $$\frac{\rho_W}{\rho_{W0}} = 1 - \frac{\rho_I}{\rho_{I0}} - \frac{\rho_{Gd}}{\rho_{Gd0}} \tag{14}$$

$$\text{Var}(\rho_W) = \frac{\rho_{W0}^2}{\rho_{I0}^2}\text{Var}(\rho_I) + \frac{\rho_{W0}^2}{\rho_{Gd0}^2}\text{Var}(\rho_{Gd}) + \frac{2\rho_{W0}^2}{\rho_{I0}\rho_{Gd0}}\text{Cov}(\rho_I, \rho_{Gd}) \tag{15}$$

Substituting $\rho_{W0}=1.00$ g/cm$^3$, $\rho_{I0}=4.93$ g/cm$^3$, and $\rho_{Gd0}=7.90$ g/cm$^3$, one can derive $$\delta(\rho_W) = \sqrt{\frac{1.00}{24.30}\text{Var}(\rho_I) + \frac{1.00}{62.41}\text{Var}(\rho_{Gd}) + \frac{2.00}{38.95}\text{Cov}(\rho_I, \rho_{Gd})} \tag{16}$$

The noise in water map is only a fraction of that in iodine and gadolinium map.

In the above non-limiting examples, a figure-of-merit (FOM) was derived to predict the overall noise magnification, and a bias analysis was performed to evaluate the impact on bias when the prior was inaccurate. FOMs were 0.75~1.21 V.S. 0.02~0.04 and 2.52~6.82 V.S. 0.05~0.16 in two- and three-material decompositions, without and with the prior. Accordingly, averaged noise levels were reduced by 51.1-63.6% (iodine) and 98.6-99.1% (water), and 25.2-70.4% (iodine), 39.8-79.7% (gadolinium), and 98.8-99.8% (water) in two- and three-material decompositions with the prior. When the prior was inaccurate, the maximum quantification bias of iodine was below 0.05 mg/cc in two-material decomposition, and that of iodine and gadolinium was below 0.20 and −0.04 mg/cc in three-material decomposition.

The present invention has been described in accordance with the embodiments shown, and one of ordinary skill in the art will readily recognize that there could be variations to the embodiments, and any variations would be within the spirit and scope of the present invention. Accordingly, many modifications may be made by one of ordinary skill in the art without departing from the spirit and scope of the appended claims.

The invention claimed is:

1. A method for performing material decomposition using a computed tomography (CT) system, the steps comprising:
   a) acquiring CT imaging data of an object including data subsets corresponding to at least two different energy spectral bins;
   b) using the CT imaging data at each of the at least two different energy spectral bins to form a series of equations for basis material decomposition;
   c) using a general physical constraint within the series of equations, wherein the general physical constraint quantifies how each basis material in the object is mixed together to form the object and wherein the general physical constraint is determined using
      reference data of predetermined parameters based on at least one of existing data or empirical measurements that are independent of multi-energy CT measurements;
   d) determining at least one basis material density of the object using the general physical constraint and the CT imaging data; and
   e) generating an image of the object using the CT imaging data and the mass densities of the at least one basis material.

2. The method of claim 1, further comprising performing at least one of: a multi-energy CT imaging acquisition to acquire the reference data from the object, or a multi-energy CT imaging acquisition to determine a series of equations for basis material decomposition.

3. The method of claim 1, wherein the reference data includes a lookup table or mathematical equations correlated to basis material composition in the object.

4. The method of claim 1, wherein the reference data indicates a general physical constraint that quantifies how basis materials are mixed to form the object.

5. A computed tomography (CT) imaging system comprising:
   at least one x-ray source configured to emit x-rays at a plurality of energy levels toward an object to be imaged;
   at least one detector configured to receive x-rays that are attenuated by the object;
   a data acquisition system (DAS) connected to the at least one detector to receive an indication of received x-rays at the plurality of energy levels;
   a computer system coupled to the DAS to receive the indication of the received x-rays at the plurality of energy levels and programmed to:
   a) acquire CT imaging data corresponding to each of at least two different energy spectral bins;
   b) use the CT imaging data at each of the last least two different energy spectral bins to form a series of equations for basis material decomposition;
   c) use a general physical constraint within the series of equations, wherein the general physical constraint quantifies how each basis material in the object is mixed together to form the object and wherein the general physical constraint is determined using
      reference data of predetermined parameters based on at least one of:
   existing data, or empirical measurements, that are independent of multi-energy CT measurements;

d) determine at least one basis material density of the object using the physical constraint and the CT imaging data; and e) generate an image of the object using the CT imaging data and the mass densities of the at least one basis material.

6. The system of claim 5, wherein the computer system is further programmed to perform at least one of: a multi-energy CT imaging acquisition to acquire the reference data from the object, or a multi-energy CT imaging acquisition to determine a series of equations for basis material decomposition.

7. The system of claim 5, wherein the reference data includes a lookup table or mathematical equations correlated to basis material composition in their mixture.

8. The system of claim 5, wherein the reference data indicates a general physical constraint that quantifies how basis materials are mixed to form the object.

* * * * *